United States Patent [19]

Bres et al.

[11] Patent Number: 4,935,526

[45] Date of Patent: Jun. 19, 1990

[54] PROCESS FOR THE PURIFICATION OF PEPTIDES

[75] Inventors: Hervé Bres, Lyons; Christian Gervais, Villeurbanne; Jean-Pierre Casati, Grigny, all of France

[73] Assignee: Rhone-Poulenc Chimie, Courbevoie Cedex, France

[21] Appl. No.: 333,238

[22] Filed: Apr. 5, 1989

[30] Foreign Application Priority Data

Apr. 6, 1988 [FR] France .................. 88 04516

[51] Int. Cl.$^5$ .................................... C07D 207/09
[52] U.S. Cl. ................................................ 548/533
[58] Field of Search .................................... 548/533

[56] References Cited

U.S. PATENT DOCUMENTS 4,465,626 8/1984 Sklavounos ..................... 549/88
4,720,554 1/1988 Irie et al. ......................... 548/533

FOREIGN PATENT DOCUMENTS 0168769 1/1986 European Pat. Off.
0279716 8/1988 European Pat. Off.

OTHER PUBLICATIONS

Biopolymers, vol. 1, pp. 517–525 (1963).
Journal of Organic Chemistry, vol. 37, No. 2, pp. 327–329 (1972).
Synthesis of ACE Inhibitors, Peptides Funct. Proc. Am. Pept. Symp. 9th pp. 787–790 (1985).

*Primary Examiner*—Joseph Paul Brust
*Assistant Examiner*—MarySue Howard
*Attorney, Agent, or Firm*—Finnegan, Henderson, Farabow, Garrett and Dunner

[57] ABSTRACT

A process for the purification and extraction of the dipeptide ε-tri-fluoroacetyllysylproline from a saturated aqueous solution of salt containing the dipeptide, at least one polypeptide and at least one isolated amino acid, by a series of successive extractions with a primary alcohol or a primary alcohol/aprotic solvent mixture.

21 Claims, No Drawings

PROCESS FOR THE PURIFICATION OF PEPTIDES

The present invention relates to a process for the purification of the dipeptide ε-trifluoroacetyllysylproline from aqueous solutions obtained during its preparation; it relates more particularly to the purification of ε-trifluoroacetyl-L-lysyl-L-proline.

The dipeptide, ε-trifluoroacetyllysylproline, is a starting material used in the synthesis of a hypertensive agent described in European Patent No. 168,769. Since it has a pharmaceutical use, this dipeptide must be presented in an extremely pure form, free from (1) polypeptide compounds containing more than two amino acids, (2) isolated amino acids and (3) salts.

The process for preparing the dipeptide ε-trifluoroacetyllysylproline requires several steps. For example, in a first step starting with lysine, the amine group situated at the ε-position is regioselectively protected.

The regioselective protection of the ε-group is carried out by means of the use of trifluoroacetic acids esters, as described, for example, in European Patent No. 279716. In European Patent No. 279716, a process is described for the $N^\omega$-trifluoroacetylation of α,ω-diamino acids with a linear alkyl trifluoroacetate, the reaction preferably taking place in an alcohol containing 1 to 5 carbon atoms, and still more preferably in the alcohol which has been used for preparing the alkyl trifluoroacetate. The reaction can also take place in an excess of alkyltrifluoroacetate. The $N^\epsilon$-trifluoroacetylated lysine is readily separated from the reaction medium and purified in a manner known per se by any process, for example by recrystallization.

At present, the only known way of obtaining the dipeptide in pure form is to prepare it in a form doubly protected by a benzyloxycarbonyl group on the amine group situated at the α-position of the lysine and a trifluoroacetyl group on the amino group situated at the ε-position. This protected dipeptide is purified, since it crystallizes easily. By hydrogenolysis, the protected dipeptide yields the desired dipeptide in pure form and with readily distillable by-products. The drawback of this method is chiefly its expense, due to costs of starting materials and to the need for the additional stages of protection and deprotection of the amine group situated at the α-position.

The only method for preparing the dipeptide from trifluoroacetylated lysine which can be economically envisaged at present consists in using phosgene, which is an inexpensive reagent. Phosgene enables the amine group situated at the α-position to be protected and also activates the carboxyl group, which enables peptide condensation yields in the order of 95 to 98% of dipeptide to be obtained.

$N^\epsilon$-Trifluoroacetylated lysine is condensed with phosgene by a process described, for example, by SELA, ARNON and JACOBSON in Biopolymers, vol. 1, 517–525 (1963). According to this process, $N^\epsilon$-trifluoroacetylated lysine is brought into contact with phosgene in a polar aprotic solvent, at a temperature of approximately 50° C., to form $N^\epsilon$-trifluoroacetyl-$N^\alpha$-carboxyl-L-lysine anhydride.

Proline in its sodium form is emulsified in an acetonitrile/water mixture, and then brought into contact with $N^\epsilon$-trifluoroacetyl-$N^\alpha$-carboxyl-L-lysine anhydride according to the process described by KATAKAI in *J. Org. Chem.*, Vol. 37, No. 2, p. 327–329 (1972).

As described in "Large Scale N-carboxy Anhydride preparation Of Ala-Pro and ε-(TFA)-Lys-pro," Synthesis of ACE inhibitors, Peptides funct., Proc. am. pept. Symp. 9th, 1985, 787–790, at the end of the reaction, there is obtained the trifluoroacetylated lysine-proline dipeptide in aqueous solution, mixed with (1) polypeptides of which the majority consists predominantly of tripeptide (TFA)-lysine-(TFA)-lysine-proline, (2) free proline, (3) salts, in particular sodium sulfate, (4) sodium chloride and (5) traces of (TFA)-lysine.

This solution contains the dipeptide at a concentration of between 2 and 10% by weight.

The dipeptide is an extremely delicate compound, which cannot withstand either alkaline pH, which results in hydrolysis of the trifluoroacetamide group, or a temperature rise, which accelerates formation of diketopiperazine by internal cyclization.

The production of the dipeptide in the pure state from crude solutions is a difficult problem which has not hitherto been solved, since the by-products formed during its preparation have very similar properties and have been found to be difficult to separate.

The present invention has made it possible to solve the problems of the prior art regarding the extraction of the dipeptide in substantially pure form from its reaction medium.

The present invention relates to a process for the purification and extraction of the dipeptide ε-trifluoroacetyllysylproline from a saturated aqueous solution of a salt containing the dipeptide, at least one polypeptide and at least one isolated amino acid, comprising the step of separating the dipeptide from the other compounds by a series of successive extractions with an extraction solution containing a primary alcohol or a mixture of primary alcohol and aprotic solvent.

Preferably, the ε-trifluoroacetyllysylproline is extracted from a saturated aqueous solution used in the preparation of the dipeptide. Preferably, the successive extractions are selective countercurrent extractions.

The saturated aqueous solution is a saturated salt solution, for example, of sodium chloride, potassium chloride or sodium sulfate.

The primary alcohol is preferably chosen from those containing 3 to 6 carbon atoms.

There may be mentioned, without limitation:
neopentyl alcohol,
1-hexanol,
2-methyl-1-propanol,
2-methyl-1-butanol,
2-pentanol, and
butanol.

It is most preferable to use 1-butanol.

The aprotic solvent is preferably selected from:
ethyl acetate,
acetonitrile,
ethers,
toluene, and
alkanes, preferably alkanes containing 6 to 8 carbon atoms.

One of the series of successive extractions referred to above can comprise the selective extraction of polypeptide(s). The selective extraction of the polypeptide(s) is preferably carried out at a pH of from 4 to 7, and more preferably at a pH of approximately 5.

The series of successive extractions may also involve the extraction of dipeptide from a solution depleted of polypeptide or the simultaneous extraction of di- and polypeptides. The extraction of the dipeptide from a solution depleted of polypeptide, or the simultaneous extraction of the di- and polypeptides, is preferably carried out at a pH of from 1 to 4, and more preferably from 1 to 3.

The percent by volume of the aprotic solvent, based on the total volume of aprotic solvent and alcohol contained in the extraction solution, is preferably from 0, when the pure alcohol is used, to 80%. The percent by volume of the aprotic solvent, based on the total volume of aprotic solvent and alcohol contained in the extraction solution, is more preferably approximately 50% when ethyl acetate and butanol are used together.

The extraction can be carried out equally well by either first extracting the polypeptides and then the dipeptide without carrying over the free amino acids, chiefly proline, or, by first separating the proline and then extracting the polypeptides and the dipeptide.

Thus, according to a first preferred process of implementation, the initial step is to remove the polypeptides. Butanol is used as the alcohol. It is preferable to perform a series of successive extractions with butanol or a butanol/ethyl acetate solution, preferably at a pH of from 4 to 7, and more preferably at a pH of approximately 5, of the aqueous solution which contains the dipeptide and is saturated with sodium chloride. The ratio by volume of the extracting butanolic solution to the extracted aqueous solution is preferably from 0.02:1 to 1:1. The butanolic extract contains, depending on the number of extractions performed, at least 90% of the polypeptides that were present in the aqueous phase.

In a second step, the dipeptide is recovered by an extraction of the aqueous phase with the butanolic solution, preferably at an acidic pH from 1 to 4, and more preferably from 1 to 3. Preferably, the ratio by volume of the butanolic phase in this second step to the aqueous phase is equal to 1:1 when a single extraction is performed, or equal to a ratio ranging from 0.02:1 to 0.5:1 when several successive extractions are performed. The isolated amino acids, such as proline, are left in the aqueous phase, which is discarded. The degree of extraction of the dipeptide advantageously can reach 95%. The resulting butanolic solution is neutralized by adding aqueous bicarbonate solution.

In a third step, a vacuum distillation is performed at a temperature below 30° C. The salts precipitate and are filtered off, leaving behind a solution of dipeptide in butanol.

This solution can be used as it is, or the dipeptide can be isolated by precipitation by means of a linear or branched alkane such as heptane, isooctane, pentane or methylcyclohexane; an ether such as methyl tert-butyl ether or diisopropyl ether; an ester such as ethyl acetate; or a ketone such a methyl isobutyl ketone.

According to a second preferred embodiment of the present invention, the isolated amino acid(s) are removed first, after which the polypeptide(s) are removed.

In this embodiment, the combination of dipeptide and polypeptide is extracted with a butanolic solution, preferably at a pH of from 1 to 7, and more preferably from 1 to 3.

The ratio of the volume of the butanolic extracting solution to the extracted saline aqueous solution is preferably from 1:1 to 10:1. The free amino acids, such as proline, in particular, remain in the aqueous solution, which is discarded.

In a second step, the butanolic solution containing the dipeptide and the polypeptides is extracted with an acidic aqueous solution, preferably at a pH of from 4 to 7, and more preferably approximately 5. The volume of the extracting solution relative to the butanolic solution is preferably from 1 to 30.

The dipeptide remains in aqueous solution whereas the tripeptide preferably passes into the butanolic solution. This step is the same as that corresponding to step 1 of the first preferred embodiment of the invention described above.

The degree of the extraction of the polypeptides is approximately 90 to 95%.

In a third stage, the dipeptide is extracted from the aqueous solution with butanol preferably at a pH of from 1 to 3. This stage is identical to stage 2 of the first preferred embodiment of the invention described above.

The dipeptide is recovered by precipitation by means of an alkane.

The present invention can enable a dipeptide having a degree of purity of more than 96% in the dry state to be obtained.

The present invention will be described more completely by means of the examples which follow, which must in no case be considered to be limiting.

EXAMPLE 1

Aqueous solution to be extracted

| | |
|---|---|
| dipeptide ($\epsilon$-TFA-Lys-Pro) = | 4.53% by weight (53.5 moles) |
| tripeptide ($\epsilon$-TFA-Lys-$\epsilon$-TFA-Lys-Pro) = | 0.34% by weight (2.4 moles) |
| proline = | 0.196% by weight (6.8 moles) |
| diketopiperazine = | 0.019% by weight (0.24 moles) |
| NaCl = | saturating concentration. |

Extracting solution
32 kg of n-butanol (40 liters)
36 kg of ethyl acetate (40 liters)
17 kg of 26.4% strength aqueous solution of NaCl, which yields a solution after mixing composed of 73 kg of butanolic phase.

1-a. removal of the tripeptide

1-$\alpha$: 400 kg of saturated aqueous NaCl solution having the composition noted above are introduced into an 800-liter glazed reactor. The aqueous phase containing the dipeptide is extracted 3 times with 22 kg of the extracting solution. The agitation time is ½ hour on each occasion. After each extraction, the pH of the aqueous phase is adjusted to approximately 4.5. 90 kg of organic phase, which contains 85.3% of the tripeptide present in the initial aqueous phase, are drawn off.

| | |
|---|---|
| The aqueous phase contains | 49.8 moles of dipeptide (equivalent to 93% of the dipeptide introduced) 0.35 moles of tripeptide 5.8 moles of proline 0.01 mole of diketopiperazine. |

1-a $\beta$
Aqueous solution to be extracted
dipeptide ($\epsilon$-TFA-Lys-Pro) =     4.41% by weight -continued

| tripeptide (ε-TFA-Lys-ε-TFA-Lys-Pro) = | 0.48% by weight |
| --- | --- |
| NaCl = | saturating concentration |
| volume 160 ml, equivalent to = | 184.1 g |
| Extracting solution | |
| Mixture of n-butanol and ethyl acetate (50 vol:50 vol) saturated with a saturated solution of NaCl in water. | |

Removal of the tripeptide at pH 4.5 160 ml of solution to be extracted and 10 ml of extracting solution are introduced into a 250-ml separating funnel. The whole is agitated vigorously for 5 min and then left standing for 20 min, and the phases are finally separated.

The aqueous phase is extracted again 4 times with the same volume of organic phase.

At the end of the operation, the 5 organic phases are combined. The residual aqueous phase weighs 168 g; it contains 86% of the initial quantity of dipeptide and 1% of the initial quantity of tripeptide. The concentration of the latter is hence 50 ppm, while the ratio by weight tripeptide/dipeptide is equal to 0.11%.

1-b extraction of the dipeptide

The aqueous phase derived from the 1st extraction series (1a α) is brought to pH 2.5 by adding concentrated hydrochloric acid. The hydrochloride of the dipeptide formed is extracted 4 times with 38.5 kg of n-butanol saturated with aqueous NaCl solution.

The successive organic phases are drawn off and combined; 196 kg of organic phase, containing 96.1% of the dipeptide present in the aqueous phase derived from the 1st extraction series, are obtained.

The depleted aqueous phase contains 1.9 moles of dipeptides and 6.6 moles of proline.

1-c neutralization of the butanolic phase

The 196 kg of butanolic phase are neutralized with 76 kg of sodium bicarbonate in 5% strength aqueous solution (pH 5.6).

It is then concentrated under reduced pressure (40 mbar) at a temperature of 25° C. in the boiling vessel and 20° C. at the head of the column for 20 hours.

56 kg of concentrate are recovered containing less than 0.02% by weight of water but containing
43 moles of dipeptide
0.39 moles of tripeptide.

After concentration, the salts are removed by filtration. 89% of the dipeptide present in the butanolic phase is recovered in the butanolic phase (yield relative to the initial solution to be extracted=79.5%).

1-d α precipitation of dipeptide with heptane

The butanolic phase contains the dipeptide at a concentration of 27% weight/weight (105 ml). This solution has the following composition:
(TFA)-Lys-Pro=96.5%
Pro<0.1%
(TFA)-Lys<0.1%
Diketopiperazine=0.85%
NaCl=1.6%
(TAF)-Lys-(TAF)-Lys-Pro=0.8%

This solution, stored at −14° C. for two months, allows a portion of the dipeptide which it contains to crystallize out.

The solid is dissolved by bringing the suspension to 40° C. for 30 minutes. The homogeneous solution obtained always has the same composition; the diketopiperazine content has not changed. If a portion of the initial solution is stored at 20° C. instead of −14° C., the diketopiperazine content rises from 0.8 to 6.3% (w/w).

The solution which has not changed is diluted by adding 52.5 ml of n-heptane.

The resulting solution is then allowed to flow over the course of 1 hour into a reactor containing 640 ml of n-heptane, with vigorous agitation.

A suspension is formed, which is agitated for 30 minutes more after the addition is complete.

The solid is collected by filtration on a No. 3 sinter.

It is resuspended in 70 ml of a 10% strength (by volume) solution of ethyl acetate in n-heptane, drained again and then washed twice with 70 ml of n-heptane.

The mother liquors contain 1.5% of the dipeptide introduced. The solid, dried under vacuum, is obtained in an overall yield of 78.3%. This composition is as follows:

| (TFA)-Lys-Pro = | 82.3% |
| --- | --- |
| H₂O = | 1.7% |
| Ethyl acetate = | 0.2% |
| n-Heptane = | 5.7% |
| NaCl = | 2.1% |
| Diketopiperazine = | 3.9% |
| Tripeptide = | 0.9% |
| n-Butanol = | 5.7% |
| | =102.5% |

1-d β precipitation of the dipeptide with isopropyl ether

An aliquot of the solution (containing 27% dipeptide, weight/weight) is stored at +4° C./+20° C. for 75 days.

Its composition is then as follows:
(TFA)-Lys-Pro=24.5% weight/weight butanolic solution
Diketopiperazine/(TFA)-Lys-Pro=10.8% weight/weight The following are introduced successively into a 1 liter pyrex reactor at 22° C.:
700 ml of diisopropyl ether
  with agitation (200 revolutions/minute), 105 ml (97.18 g) of butanolic solution, introduced in a regular manner in the course of 1 hour.

The suspension of dipeptide is agitated for a further 15 minutes, and is then drawn off via the bottom valve and transferred to a No. 3 porosity glass sinter 100 mm in diameter. Drainage is rapid.

The solid is resuspended three times with 75 ml of diisopropyl ether, drained thoroughly and then dried in an oven at room temperature under 0.2 torr.

| RESULTS: Yield of the precipitation: 98% | |
| --- | --- |
| Composition of solid | |
| (TFA)-Lys-Pro = | 84.0% w/w |
| Diketopiperazine = | 4.5% w/w |
| Tripeptide = | 0.8% w/w |
| n-Butanol = | 1.7% w/w |
| Diisopropyl ether = | 5.3% w/w |
| Water = | 1.5% w/w |
| NaCl = | 2.0% w/w |

EXAMPLE 2

This example serves to demonstrate the feasibility of the second means of implementation of the invention; it was not optimized with respect to the pH of the extraction.

Aqueous solution to be extracted:

| | |
|---|---|
| dipeptide (ε-TFA-Lys-Pro) = | 4.95% weight/weight (73 mmol) |
| tripeptide = (ε-TFA-Lys-ε-TFA-Lys-Pro) | 0.18% weight/weight (1.6 mmol) |
| proline = | 0.32% weight/weight (14 mmol) |
| diketopiperazine | <0.01% weight/weight |
| NaCl = | saturating concentration |
| pH = | 5.5 |
| Extracting solution: | |
| n-butanol = | 5 liters |
| 26.4% strength aqueous NaCl solution = | 1 kg |
| which yields after mixing a butanolic phase weighing 4.5 kg. | |

2-a extraction of the peptides 500 g of aqueous solution to be extracted, having the composition noted above, are introduced into a 1 liter pyrex reactor.

This aqueous phase is extracted 10 times with 0.5 liter of the extracting solution. The agitation time is 3 minutes on each occasion, while the settling time is 15 minutes.

The butanolic phase weighs 4420 g in total and contains:
- 67.5 mmol of dipeptide (92% of the dipeptide introduced)
- 1.54 mmol of tripeptide
- 0.014 mmol of proline.

2-b concentration of the butanolic phase

The butanolic phase is concentrated by evaporation of the butanol under vacuum (quantitative yield). After filtration of the NaCl precipitate, a solution of dipeptide at a concentration of 20.4% by weight in butanol is obtained.

2-c removal of the tripeptide

A 64 g portion of the organic solution obtained above by concentration, containing:
- 13 g of dipeptide (38 mmol)
- 0.93 g of tripeptide (1.65 mmol) is extracted with 6×75 ml and 9×150 ml of saturated brine at pH 3.

The combined aqueous extracts, having a total mass of 2420 g, contain:
- 12.5 g of dipeptide (equivalent to 96% of the 13 g present in the 64 g portion of the organic solution)
- 0.08 g of tripeptide.

2-d Concentration

The aqueous phase obtained above is concentrated at 30° C. by vacuum distillation, to a content of 5% of dipeptide.

2-e isolation of the dipeptide

This is carried out according to Example 3, operations 3d to 3g inclusive.

EXAMPLE 3

Aqueous solution to be extracted:

| | |
|---|---|
| dipeptide | 5.75% by weight |
| tripeptide | 0.36% by weight |
| proline | 0.60% by weight |
| NaCl | saturating concentration |
| pH | 5.5. |

Extracting solution:
n-butanol saturated by contact with a brine solution.

3-a extraction of the peptides

The extraction is carried out in countercurrent fashion by means of a KUHNI brand agitated column 60 mm in diameter, comprising 40 compartments agitated by 190 revolutions per minute (total height 3.88 m).

The aqueous phase is injected at the top of this column, while the butanolic phase is injected at the base, at a flow rate 2.65-fold greater.

An organic extract containing 86.4% of the dipeptide introduced, at a concentration of 1.8% by weight, is obtained. The concentration of the tripeptide is then 0.15%.

3-b concentration of the butanolic extract

The butanolic extract is concentrated at 30° C. under vacuum. The sodium chloride which precipitates is removed by filtration; a solution is then obtained containing 86.4% of the dipeptide initially introduced in the form of an aqueous solution to be extracted.

3-c removal of the tripeptide

The same agitated column is used for removing the tripeptide.

The above butanolic solution containing 3.68% of dipeptide is injected at the base of the column, while a saturated NaCl solution having a pH of 4.4 is introduced at the top at a flow rate 2.3fold greater.

At the base of the column, the aqueous phase containing 86.4% of the peptide introduced initially at stage 3 is collected. This solution, having a dipeptide concentration of 1.6%, contains only 0.029% of tripeptide by weight.

The tripeptide reappears in toto in the butanolic effluent having a tripeptide concentration equal to 0.29% by weight.

3-d extraction of the dipeptide into an organic medium

The aqueous solution saturated with NaCl obtained above is concentrated under a vacuum of 1 torr at 25° C.

From 3.357 kg of this solution containing 1.6% of dipeptide, 0.910 kg of aqueous phase containing 5.9% weight/weight of dipeptide, equivalent to 53.69 g of dipeptide, is obtained after filtration of the sodium chloride precipitate.

This aqueous phase is extracted 15 times with 450 ml of a 20% strength (volume/volume) solution of ethyl acetate in butanol.

The organic extracts contain 44 g of dipeptide, equivalent to an extraction yield of 81.8%, corresponding to 70.7% of the dipeptide introduced.

3-e concentration of the butanolic extract

The above solution, weighing 8840 g and containing 44 g of dipeptide, is concentrated under 0.5 torr at 25° C. The butanol/water azeotrope is removed and the formation of a sodium chloride precipitate is observed, this being removed by filtration.

The concentrated solution obtained has a mass of 192 g, contains 44 g of dipeptide (concentration 23%) and 0.3 g of NaCl.

3-f precipitation of the dicetide with a non-solvent

The concentrated butanolic phase is allowed to flow into a agitated reactor containing 1 liter of heptane at 23° C., thereby generating a precipitate.

The precipitate is filtered off and then dried to a constant weight of 45.4 g. The product is in the form of a powder.

A 38 g portion of this powder is resuspended in a mixture composed of 450 ml of heptane and 50 ml of ethyl acetate.

After 2 hours of agitation, the solid is isolated by filtration on a No. 4 porosity glass sinter. It is washed with 2×100 ml of a heptane/ethyl acetate (90:10) mixture and dried under 1 torr for 6 hours at room temperature.

The weight of the solid obtained is 36.78 g, its assay 92%. The precipitation yield is 91.8%.

The overall yield from the aqueous solution to be extracted is 64.9%.

characteristics of the solid dipeptide obtained

|  |  | Method |
| --- | --- | --- |
| dipeptide | 92.0% by weight | HPLC |
| tripeptide | 1.8% by weight | HPLC |
| diketopiperazine | 1.0% by weight | HPLC |
| proline | not detected | HPLC |
| NaCl | 1.76 | argentimetric $CL^-$ assay |
| $H_2O$ | 2.4 |  |
| butanol | 2 | chromatography |
| heptane | 0.54 | gas chromatography |
| ethyl acetate | 0.52 |  |

.Assay of acidity with $Bu_4N^+OH^-$ 1st jump (COOH): 2.72 equivalents/kg (theory 2.95) second jump ($NHCOCF_3$): 2.72 equivalents/kg equivalent potentiometric titer of 92.2%.
.$[\alpha]_D^{21} = -36.5°$ (1% strength solution in EtOH).
.Melting point 105° C.
.Identity confirmed by mass spectrometry and 1− and 2− dimensional $^{13}C$ and $^1H$ NMR spectrometry (360 $MH_z$, solvent $CH_3OD$).

What is claimed:

1. A process for the purification and extraction of the dipeptide ε-trifluoroacetyllysylproline from a saturated aqueous solution of a salt containing said dipeptide, at least one polypeptide and at least one isolated amino acid, comprising the step of separating the dipeptide from the other compounds by a series of successive extractions with an extraction solution containing a primary alcohol or a mixture of primary alcohol and aprotic solvent.

2. The process as claimed in claim 1, wherein the extraction solution contains a primary alcohol having 3 to 6 carbon atoms.

3. The process as claimed in claim 2, wherein the primary alcohol is selected from the group consisting of butanol, neopentyl alcohol, hexanol, 2-methylpropanol, 2-methylbutanol, and pentanol.

4. The process as claimed in claim 3, wherein the alcohol is 1-butanol.

5. The process as claimed in claim 1, wherein the aprotic solvent is selected from the group consisting of ethyl acetate, acetonitrile, ethers, toluene and alkanes.

6. The process as claimed in claim 5, wherein said alkane contains 6 to 8 carbon atoms.

7. The process as claimed in claim 1, wherein the extraction solution contains 20 to 100% by volume of primary alcohol and 0 to 80% by volume of aprotic solvent, both based on the total volume of primary alcohol and aprotic solvent.

8. The process as claimed in claim 2, wherein the solution contains a mixture of butanol and ethyl acetate containing 50% by volume of butanol.

9. The process as claimed in claim 1, wherein one of the series of successive extractions comprises the selective extraction of said at least one polypeptide at a pH of from 4 to 7.

10. The process as claimed in claim 9, wherein the selective extraction of the polypeptide is carried out at pH of approximately 5.

11. The process as claimed in claim 1, wherein one of the series of successive extractions comprises the extraction of the dipeptide at a pH of from 1 to 4.

12. The process as claimed in claim 11, wherein said extraction of the dipeptide is carried out at a pH of from 1 to 3.

13. A process for the precipitation of the dipeptide ε-trifluoroacetyllysylproline from a butanolic solution of said dipeptide, comprising the step of adding to said solution a solvent selected from alkanes, ethers, ketones and esters.

14. A process as claimed in claim 13, wherein the solvent is an ether.

15. A process for the purification and extraction of the dipeptide ε-trifluoroacetyllysylproline from a saline aqueous solution containing the dipeptide, at least one polypeptide and proline, comprising the steps of:
(1) performing a series of successive extractions with a butanol-based solvent at a pH ranging from 4 to 7, to extract said at least one polypeptide selectively;
(2) extracting the residual aqueous solution from the first step with a butanol-based solution at a pH ranging from 1 to 4, and removing the residual aqueous phase containing proline;
(3) neutralizing the remaining butanolic solution containing said dipeptide with an aqueous alkaline solution; and
(4) performing a distillation of said neutralized butanolic solution under reduced pressure.

16. A process as claimed in claim 15, wherein after said distillation step, a further step is performed comprising precipitating the dipeptide by adding an alkane or an ether.

17. A process as claimed in claim 15 wherein said saline aqueous solution contains at least one additional amino acid and at least one additional inorganic salt.

18. A process as claimed in claim 15, wherein the selective extractions of said at least one polypeptide with a butanol-based solvent is performed at a pH of 5, and further wherein the residual aqueous solution is extracted at a pH of from 1 to 3.

19. A process for the purification and extraction of the dipeptide ε-trifluoroacetyllysylproline from an aqueous solution containing the dipeptide, at least one polypeptide, proline and, at least one inorganic salt, comprising the steps of:
(1) performing an extraction with a butanol-based solvent at a pH of from 1 to 4, and removing an aqueous solution containing proline;
(2) extracting the dipeptide and said at least one salt with an acidic aqueous solution at a pH of between 4 and 7 and removing the polypeptide in the organic solution; and (3) selectively extracting the dipeptide with a butanolic solution.

20. A process as claimed in claim 19, wherein after said step (3), a further step is performed comprising precipitating the dipeptide from the butanolic solution with a alkane or an ether.

21. A process as claimed in claim 19, wherein the removal of the aqueous solution containing proline is accomplished by extractions with a butanol-based solvent at a pH from 1 to 3, and wherein the extraction of the dipeptide and said at least one salt is performed at a pH of 5.

* * * * *